United States Patent [19]

Dornoff

[11] Patent Number: 5,968,493

[45] Date of Patent: Oct. 19, 1999

[54] HAIR CARE COMPOSITION

[75] Inventor: Jeffrey M. Dornoff, Grand Rapids, Mich.

[73] Assignee: Amway Corportion, Ada, Mich.

[21] Appl. No.: 08/959,626

[22] Filed: Oct. 28, 1997

[51] Int. Cl.$^6$ .............................. A61K 7/06; A61K 7/11; A61K 31/74

[52] U.S. Cl. .................. 424/70.1; 424/70.11; 424/70.12; 424/70.15; 424/78.03

[58] Field of Search ................................ 424/70.1, 70.12, 424/70.15, 70.11, 78.03

[56] References Cited

U.S. PATENT DOCUMENTS

| | | |
|---|---|---|
| 3,503,895 | 3/1970 | Whelan . |
| 3,950,260 | 4/1976 | Eldib . |
| 3,969,500 | 7/1976 | Kennerley . |
| 3,980,769 | 9/1976 | Ghilardi et al. . |
| 4,022,731 | 5/1977 | Schmitt . |
| 4,228,048 | 10/1980 | Tesdahl . |
| 4,260,528 | 4/1981 | Fox et al. . |
| 4,284,534 | 8/1981 | Ehrlich . |
| 4,414,144 | 11/1983 | Liebowitz et al. . |
| 4,434,087 | 2/1984 | Hampson et al. . |
| 4,472,297 | 9/1984 | Bolich, Jr. et al. . |
| 4,576,744 | 3/1986 | Edwards et al. . |
| 4,788,006 | 11/1988 | Bolich, Jr. et al. . |
| 4,983,383 | 1/1991 | Maksimoski et al. . |
| 5,034,218 | 7/1991 | Duvel . |
| 5,114,706 | 5/1992 | Duvel . |
| 5,160,730 | 11/1992 | Dubief et al. . |
| 5,176,898 | 1/1993 | Goldberg et al. . |
| 5,198,209 | 3/1993 | Zhou et al. . |
| 5,380,528 | 1/1995 | Alban et al. . |
| 5,409,695 | 4/1995 | Abrutyn et al. . |
| 5,420,118 | 5/1995 | Alban et al. . |
| 5,567,426 | 10/1996 | Nadaud et al. . |
| 5,599,800 | 2/1997 | Candau et al. . |
| 5,656,257 | 8/1997 | Fealy et al. . |

FOREIGN PATENT DOCUMENTS

| | | |
|---|---|---|
| 0 013 836 | 8/1980 | European Pat. Off. . |
| 0 051 983 | 5/1982 | European Pat. Off. . |
| 0 071 413 | 2/1983 | European Pat. Off. . |
| 0 071 414 | 2/1983 | European Pat. Off. . |
| 0 089 213 | 9/1983 | European Pat. Off. . |
| 0 555 690 A1 | 8/1993 | European Pat. Off. . |
| 1071660 | 6/1967 | United Kingdom . |
| 1073655 | 6/1967 | United Kingdom . |
| 1250614 | 10/1971 | United Kingdom . |
| 1270040 | 4/1972 | United Kingdom . |
| 1380402 | 7/1972 | United Kingdom . |
| 1429639 | 3/1976 | United Kingdom . |
| 1460893 | 1/1977 | United Kingdom . |
| 1471406 | 4/1977 | United Kingdom . |
| 1512355 | 6/1978 | United Kingdom . |
| 1576946 | 10/1980 | United Kingdom . |
| 1584127 | 2/1981 | United Kingdom . |
| 2 095 276A | 9/1982 | United Kingdom . |
| 2 103 236A | 2/1983 | United Kingdom . |
| 2 104 913A | 3/1983 | United Kingdom . |
| 2 105 325A | 3/1983 | United Kingdom . |
| 2 108 520A | 5/1983 | United Kingdom . |
| 2 126 243A | 3/1984 | United Kingdom . |
| 2 130 236A | 5/1984 | United Kingdom . |
| WO 83/03621 | 10/1983 | WIPO . |
| WO 96/32919 | 10/1996 | WIPO . |

*Primary Examiner*—Carlos A. Azpuru
*Attorney, Agent, or Firm*—G. Peter Nichols; Brinks, Hofer, Gilson & Lione

[57] ABSTRACT

A stable hair care composition comprising from about 1.00% to about 80.00% by weight of one or more surfactants selected from the group consisting of anionic, nonionic, cationic and zwitterionic surfactants and mixtures thereof; from about 0.05% to about 15.00% by weight of at least one fatty alcohol having from about 10 to about 30 carbon atoms; from about 0.10% to about 15.00% by weight of a non-volatile silicone; and from about 1.35% to about 2.70% by weight of a non-crosslinked polymeric suspending agent.

26 Claims, No Drawings

HAIR CARE COMPOSITION

BACKGROUND OF THE INVENTION

The present invention is directed to a stable hair care composition and, in particular, to a stable shampoo composition comprising a surfactant, a fatty alcohol, a non-volatile silicone, and a critical amount of a polymeric suspending agent, wherein the polymeric suspending agent is the sole suspending agent for suspending the silicone in the composition. The polymeric suspending agent is a polymer that is substantially free of any crosslinking, e.g., a non-crosslinked polymer. The present invention also relates to a method of suspending silicone in a water-based shampoo matrix using a non-crosslinked polymeric suspending agent.

The use of silicones in shampoo compositions has been disclosed in a number of different patents: U.S. Pat. No. 3,964,500 to Drakoff, U.S. Pat. No. 4,364,837 to Pader, U.S. Pat. Nos. 4,788,006 and 4,902,499 to Bolich, Jr. et al., U.S. Pat. No. 5,034,218 to Duvel, and U.S. Pat. No. 5,409,695 to Abrutyn et al. A major problem associated with formulating a shampoo composition containing silicone is the instability of the composition. A particularly difficult problem in silicone-containing shampoos is that of keeping a dispersed, insoluble, non-volatile silicone material suspended in stable form while retaining the performance properties of the shampoo.

Attempts to overcome such instability have been made. For example, it is known to stabilize silicone by using one or more of triethanolamine or triethanolamine compounds such as triethanolamine stearate, ethylene glycol distearate and stearamine. Additionally, U.S. Pat. No. 5,034,218 teaches that anionic surfactants and cationic conditioning agents are compatible, when combined with an anionic polymeric suspending agent, to suspend non-volatile silicone in the composition. In particular, this patent discloses a stable conditioning shampoo composition having an anionic surfactant and a cationic quaternary nitrogen-containing conditioning agent with a non-volatile silicone suspended therein using an anionic, crosslinked polymeric suspending agent such as a crosslinked polyacrylic acid suspending agent. The polyacrylic acid is an anionic crosslinked material and, more importantly, is not the only suspending agent. Other suspending agents such as distearyldimonium chloride, distearyl dimethyl ammonium chloride and dicetyl dimethyl ammonium chloride are also included.

A publicly available shampoo contains a non-crosslinked material, namely an acrylate/steareth-20 methacrylate copolymer, as a thickener. It is believed that this copolymer is present in minimal amounts of less than 1.00% by weight. Thus, the copolymer is not present at the critical level necessary for enhanced stability according to the present invention. This shampoo also contains other suspending agents such as triethanolamine stearate, ethylene glycol distearate and stearamine.

Rohm & Haas discloses the use of an acrylate copolymer, sold under the trade name Aculyn® 33, in an anti-dandruff shampoo. Rohm & Haas also discloses the use of an acrylate/steareth-20 methacrylate copolymer, sold under the trade name Aculyn® 22, in another anti-dandruff shampoo. These shampoos, however, do not contain any silicone. Moreover, the level of the acrylate and acrylate/steareth-20 methacrylate copolymers is less than the level found to be critical in the present invention.

SUMMARY OF THE INVENTION

In accordance with the present invention, it has been found, surprisingly, that a shampoo composition containing a surfactant, a fatty alcohol, and a non-volatile silicone material has extended product stability and excellent cleansing properties when combined with a critical amount of a polymeric suspending agent that is substantially free of any crosslinking as the sole suspending agent for the silicone. The phrase "substantially free of any crosslinking" is used to describe a polymeric suspending agent being crosslinked in an amount less than about 1.00% and, preferably, less than about 0.10%. The phrase "sole suspending agent" is used to mean that the composition is free of (i.e., does not contain) known suspending agents such as long chain acyl derivatives as described in U.S. Pat. No. 4,704,272 to Oh et al. and U.S. Pat. No. 4,741,855 to Grote et al., cellulosic thickeners as described in U.S. Pat. No. 4,788,006 to Bolich et al., dipthalic acid amides as described in U.S. Pat. No. 5,188,823 to Shapiro et al. and U.S. Pat. No. 5,015,415 to Goze et al., all of which are incorporated herein by reference, and other traditional suspension systems such as triethanolamine stearate, clays and gums in amounts sufficient to stabilize the silicone.

In one aspect, the present invention is a shampoo composition comprising from about 1.00% to about 80.00% by weight of one or more surfactants selected from the group consisting of anionic, nonionic, cationic and zwitterionic surfactants and mixtures thereof; from about 0.05% to about 15.00% by weight of at least one fatty alcohol having from about 10 to about 30 carbon atoms; from about 0.10% to about 15.00% by weight of a non-volatile silicone; and from about 1.35% to about 2.70% by weight of a polymeric suspending agent that is substantially free of crosslinking. It is critical that the polymeric suspending agent be present in an amount that is at least about 1.35%, otherwise the formulation will not be stable, i.e., the composition will separate into at least two layers upon standing.

In another aspect, the present invention is a method of suspending non-volatile silicone in a shampoo composition comprising admixing an effective amount, preferably from about 1.35% to about 2.70% by weight, of a non-crosslinked polymeric suspending agent in the shampoo composition.

In yet another aspect, the present invention is a shampoo composition comprising water, one or more surfactants, a fatty alcohol, and a non-volatile silicone, wherein the improvement comprises adding from about 1.35% to about 2.70% by weight of a polymeric suspending agent that is substantially free of crosslinking to suspend the non-volatile silicone in the composition.

The above and other aspects and advantages of the present invention will become apparent from the following detailed description of the preferred embodiments. It is noted that, unless otherwise stated, all percentages given in this specification and the appended claims refer to percentages by weight of the total composition.

DETAILED DESCRIPTION OF THE PREFERRED EMBODIMENTS

The aqueous shampoo composition of the present invention generally includes at least one surfactant selected from the group consisting of anionic, nonionic, cationic and zwitterionic surfactants and mixtures thereof in an amount of about 1.00% to about 80.00% by weight of the composition; one or more fatty alcohols in the amount of about 0.05% to about 15.00% by weight of the composition; non-volatile silicone in an amount of about 0.10% to about 15.00% by weight of the composition; and a polymeric suspending agent that is substantially free of any crosslinking in the amount of about 1.35% to about 2.70% by weight of the composition.

The surfactants useful in the composition and method of the present invention include anionic, nonionic, cationic, and zwitterionic surfactants and mixtures thereof. The anionic surfactant can be any of the anionic surfactants known or previously used in the art of shampoo compositions. Suitable anionic surfactants include, but are not limited to, compounds in the classes known as alkyl sulfates, alkyl ether sulfates, alkyl ether sulfonates, alpha-olefin sulfonates, beta alkloxy alkene sulfonates, alkyl arylsulfonates, alkyl carbonates, alkyl ether carbonates, alkyl ether carboxylates, succinamates, sulfosuccinates, sarcosinates, taurates, fatty acid taurides, sulfated monoglycerides, fatty acid amino polyoxyethylene sulfates, and isothienates and combination thereof Anionic detergents that are particularly useful include alkyl and alkyl ether sulfates. The alkyl sulfates have the general formula $ROSO_3M$ and the alkyl ether sulfates have the general formula $RO(C_2H_4O)_xSO_3M$ wherein R is an alkyl or alkenyl group of about 10 to 20 carbon atoms, x is from 1 to 10 and M is a water-soluble cation such as ammonium, potassium, sodium and triethanolamine. The alkyl ether sulfates useful in the present invention are condensation products of ethylene oxide and monohydric alcohols having from about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with up to 10, and especially 2, molar proportions of ethylene oxide, and the resulting mixture of molecular species having, for example, an average of 2 moles of ethylene oxide per mole of alcohol, is sulfated and neutralized.

An especially useful anionic surfactant is a mixture of a lauryl sulfate salt, a lauryl ether sulfate salt, and a lauroyl sarcosinate salt. Other suitable anionic surfactants are described in *McCutcheon's Detergents and Emulsifiers and Surface Active Agents and Detergents* (Vol. I and II) by Schwartz, Perry and Berch, both of which are incorporated herein in their entirety by reference Nonionic surfactants can be broadly defined as compounds produced by the condensation of alkylene oxide groups (hydrophilic in nature) with an organic hydrophobic compound, which may be aliphatic or alkyl aromatic in nature. Nonlimiting examples of preferred classes of nonionic surfactants are:

1. The polyethylene oxide condensates of alkyl phenols. These compounds include the condensation products of alkyl phenols having an alkyl group containing from about 6 to 12 carbon atoms in either a straight chain or branched chain configuration with ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol and the condensation product of about 9 moles of ethylene oxide with coconut alcohol (a mixture of fatty alcohols with alkyl chains varying in length from about 10 to 14 carbon atoms).

3. The condensation products of ethylene oxide with a hydrophobic base formed by the condensation of propylene oxide with propylene glycol. The hydrophobic portion of these compounds has a molecular weight of from about 1500 to 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide.

4. The condensation of ethylene oxide with the product resulting from the reaction of propylene oxide and ethylenediamine. The hydrophobic moiety of these products consists of the reaction product of ethylenediamine and excess propylene oxide, the moiety having a molecular weight of from about 2500 to about 3000. This hydrophobic moiety is condensed with propylene oxide to the extent that the condensation product contains from about 40% to about 80% by weight of polyoxyethylene and has a molecular weight of from about 5,000 to about 11,000.

5. Semi-polar nonionic surfactant detergents include water-soluble amine oxides and phosphine oxides containing one alkyl moiety of from about 10 to 18 carbons and two moieties selected from the group consisting of alkyl groups and hydroxyalkyl groups containing from 1 to about 3 carbon atoms and water-soluble sulfoxides containing one alkyl moiety of from about 10 to 18 carbons and one moiety selected from the group consisting of alkyl groups and hydroxyalkyl groups containing from 1 to about 3 carbon atoms.

Other suitable nonionic surfactants are described in *McCutcheon's Detergents and Emulsifiers and Surface Active Agents and Detergents* (Vol. I and II) by Schwartz, Perry and Berch, both of which are incorporated herein in their entirety by reference.

Cationic surfactants may also be useful in compositions of the present invention. Nonlimiting examples of preferred classes of cationic surfactants are:

1. Quaternary ammonium-containing cationic surfactant materials of the general formula:

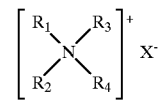

wherein $R_1$ is hydrogen, an aliphatic group of from 1 to 22 carbon atoms or an aromatic, aryl or alkylaryl group having from 12 to 22 carbon atoms, $R_2$ is an aliphatic group having from 1 to 3 carbon atoms and X is an anion selected from halogen, acetate, phosphate, nitrate and alkyl sulfate radicals. The aliphatic groups may contain, in addition to carbon and hydrogen atoms, ether linkages and other groups such as amino groups.

2. Other quaternary ammonium salts useful herein are of the formula:

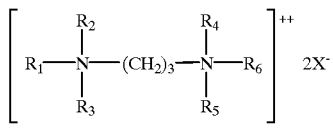

wherein R1 is an aliphatic group having from 16 to 22 carbon atoms, $R_2$, $R_3$, $R_4$, $R_5$ and $R_6$ are selected from hydrogen and alkyl groups having from 1 to 4 carbon atoms and X is an ion selected from halogen, acetate, phosphate, nitrate and alkyl sulfate radicals.

3. Salts of primary, secondary or tertiary fatty amines. The alkyl groups of such amines preferably have from 12 to 22 carbon atoms and may be substituted or unsubstituted. Examples of such amines include stearamido propyl dimethyl amine, diethyl amino ethyl stearamide, dimethyl stearamine, myristyl amine, tridecyl amine, ethyl stearylamine, ethoxylated stearylamine and dihydroxy ethyl stearylamine. Suitable amine salts include the halogen, acetate, phosphate, nitrate, citrate, lactate and alkyl sulfate salts. Such salts include stearylamine hydrochloride, stearylamine formate and stearamidopropyl dimethylamine citrate. Other suitable cationic surfactants are described in *McCutcheon's Detergents and Emulsifiers and Surface Active Agents and Detergents* (Vol. I and II) by Schwartz, Perry and Berch, both of which are incorporated herein in their entirety by reference.

The zwitterionic surfactants can be any of the zwitterionic surfactants known or previously used in the art of shampoo compositions. The zwitterionic surfactants provide major lather benefits while modifying the nature of the composition so that it is less strongly anionic. The zwitterionic surfactants useful in the present invention generally have the formula

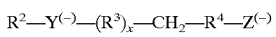

wherein $R^2$ contains an alkyl, alkenyl or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus and sulfur atoms; $R^3$ is an alkyl or monohydroxyalkyl group containing from 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is selected from the group consisting of carboxylate, sulfonate, sulfate, phosphonate and phosphate groups.

Other zwitterionic surfactants such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine and cetyl dimethyl carboxymethyl betaine, etc. The sulfobetaines may be represented by coco dimethyl sulfopropyl betaine, stearyl dimethyl sulfopropyl betaine, lauryl dimethyl sulfoethyl betaine and the like. Preferred zwitterionic surfactants are amido betaines and amidosulfo betaines, wherein the $RCONH(CH_2)_3$ radical is attached to the nitrogen atom of the betaine. An especially preferred zwitterionic surfactant is cocamidopropyl betaine. Other suitable zwitterionic surfactants are described in *McCutcheon's Detergents and Emulsifiers and Surface Active Agents and Detergents* (Vol. I and II) by Schwartz, Perry and Berch, both of which are incorporated herein in their entirety by reference.

Mixtures of anionic, nonionic, cationic and zwitterionic surfactants may also be useful in the composition and method of the present invention. An especially useful surfactant is a mixture of anionic and zwitterionic surfactants, particularly, a salt of each of alkyl sulfate, alkyl ether sulfate and sarcosinate in combination with an amido betaine.

The surfactant will generally be present in the hair care composition at a level of from about 1.00% to about 80.00%, preferably from about 5.00% to about 60.00%, more preferably from about 10.00% to about 40.00% and most preferably from about 12.00% to about 20.00%.

The hair care composition of the present invention also includes from about 0.05% to about 15.00%, preferably from about 0.10% to about 10.00% and more preferably from about 0.20% to about 5.00%, of one or more fatty alcohols. Fatty alcohols useful in the present invention are primary or secondary alcohols having from about 10 to about 26 carbon atoms, inclusive, either as single long chain lengths or as a mixture of long chain lengths in any combination. The fatty alcohols can be straight chain, branched, saturated and/or unsaturated structures. The fatty alcohols can be used alone or in combination with each other. The preferred fatty alcohols are straight chain primary alcohols having from about 12 to about 24 carbon atoms or mixtures of 12, 14, 16, 18, 20, 22 and/or 24 carbon atoms including, without limitation, lauryl, tridecyl, myristyl, cetyl, stearyl, oleyl, behenyl, arachyl, carnubyl and cetyl alcohols, and combinations thereof Especially preferred are cetyl and stearyl alcohols.

Other suitable alcohols include the fatty alcohols of the above-described carbon lengths that are ethoxylated to contain an average of about 1 to about 3, and preferably an average of about 1 or about 2, moles of ethylene oxide per mole of fatty alcohol. These may be used in place of the fatty alcohols themselves. Examples of such useful ethoxylated fatty alcohols include ethylene glycol cetyl ether, polyoxyethylene (2) stearyl ether and the like, the exemplary compounds having CTFA Dictionary names of Ceteth- 1 and Steareth-1, respectively.

The composition of the present invention also includes from about 0.10% to about 15.00%, preferably from about 1.00% to about 10.00%, and more preferably from about 1.50% to about 5.00%, by weight of a non-volatile silicone compound. The non-volatile silicones useful in the composition and method of the present invention are exemplified by the polyalkyl siloxanes, polyalkylaryl siloxanes, polyether siloxane polymers, and silicone gums.

The essentially non-volatile polyalkyl siloxanes that may be used include, for example, polydimethyl siloxanes with viscosities ranging from about 5 to 600,000 centistokes at 250° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970. Preferably, the viscosity ranges from about 350 centistokes to about 100,000 centistokes.

The essentially non-volatile polyalkylaryl siloxanes that may be used include, for example, polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid. Additionally, poly(dimethyl siloxane) (diphenyl siloxane) copolymers having a viscosity in the range of from about 10 to about 100,000 centistokes at 25° C. are useful.

The essentially non-volatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

References disclosing suitable silicones include *Silicone Compounds* distributed by Petrarch Systems, Inc., 1984. This reference is herein incorporated by reference.

Another silicone material found especially useful in the present compositions is a silicone gum. Silicone gums described by Petrarch and others, including U.S. Pat. No. 4,152,416 to Spitzer et al. and Noll, Walter, *Chemistry and Technology of Silicones,* New York, Academic Press, 1986. Also describing silicone gums are General Electric Silicone Rubber Product Data Sheets SE 30, SE 33, SE 54, and SE 76. All of these references are incorporated herein by reference. "Silicone gum" materials denote high molecular weight polydiorganosiloxanes generally having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer, and mixtures thereof.

The non-volatile silicone compound is added to the composition of the present invention in an amount sufficient to provide improved combing and improved softness to the hair. The preferred non-volatile silicone is dimethicone.

Any non-crosslinked polymer and those that have less than about 1.00% crosslinking can be used as the suspending agent in the composition and method of the present invention. The suspending agent is added to the composition of the present invention in an amount effective to suspend the non-volatile silicone material in the composition so that the composition remains stable at 120° F. for at least 30 days. It has been found that the suspending agent must be present at a minimal effective amount of at least about 1.35%. Preferably, the suspending agent is incorporated in an amount from about 1.35% to about 2.70% and more preferably from about 2.00% to about 2.30%.

To achieve optimal suspension of the non-volatile silicone, the polymeric suspending agent should generally be substantially free of crosslinking. Thus, the polymeric suspending agent either should be non-crosslinked or should be crosslinked in an amount less than about 1.00% and, preferably, less than about 0.10%. Moreover, it is desirable to use a nonionic polymeric suspending agent.

Examples of suitable polymeric suspending agents useful in the composition and method of the present invention include acrylate copolymer and acrylate/steareth-20 methacrylate copolymer, which is a polymer of the ester of methacrylic acid and steareth-20 and one or more monomers of acrylic acid, methacrylic acid or one of their simple esters. One useful suspending agent is acrylate copolymer sold under the trade name Acculyn® 33 by Rohm and Haas Company of Philadelphia, Pa. Especially useful is acrylate/steareth-20 methacrylate copolymer sold under the trade name Aculyn® 22 also by Rohm and Haas.

The composition and method of the present invention can utilize other compatible ingredients so long as they do not detract from the advantageous results of the present invention. Typically, such additional ingredients are included in an aggregate amount of less than about 10.00%, typically less than about 5.00%, and preferably less than about 3.50%. These include dyes, preservatives, fragrance, buffering agents and viscosity builders.

In another embodiment, the present invention is a hair care composition consisting essentially of a surfactant, a fatty alcohol, a non-volatile silicone and a critical amount of a non-crosslinked polymeric suspending agent, wherein the polymeric suspending agent is the sole suspending agent for suspending the silicone in the composition.

In yet another embodiment, the present invention is a hair care composition consisting of a surfactant, a fatty alcohol, a non-volatile silicone and a critical amount of a non-crosslinked polymeric suspending agent, wherein the polymeric suspending agent is the sole suspending agent for suspending the silicone in the composition To achieve the best stability, the non-crosslinked polymeric suspending agent is slowly added to the water, and the mixture is agitated until the suspending agent is dispersed. The surfactant, or surfactant mixture, is added and the mixture is heated to a temperature of about 175° F.–180° F. When the temperature reaches about 175° F., the fatty alcohol(s) is added until it is completely dispersed. The silicone is then added and the mixture is vigorously agitated until the mixture is uniform. The mixture is then cooled to about 125° F. at which time various adjuvants may be added.

The following non-limiting examples illustrate various shampoos made in accordance with the present invention:

| INGREDIENTS | WEIGHT PERCENT |
|---|---|
| Ammonium lauryl sulfate (28% active) | 25.000 |
| Ammonium laureth sulfate (25% active) | 20.000 |
| Sodium lauroyl sarcosinate (30% active) | 5.000 |
| Cocamidopropyl betaine (30% active) | 5.000 |
| Dimethicone | 2.000 |
| Cetyl alcohol | 0.200 |
| Stearyl alcohol | 0.100 |
| Acrylate/steareth-20 methacrylate copolymer (27–30% active) (Acculyn ® 22) | 7.200 |
| Water | 32.417 |
| Adjuvants | 3.083 |
| TOTAL | 100.000 |

EXAMPLES 2–6

| | EXAMPLE 2–6 (wt %) | | | | |
|---|---|---|---|---|---|
| INGREDIENTS | 2 | 3 | 4 | 5 | 6 |
| Ammonium lauryl sulfate (28% active) | 45.00 | 45.00 | 45.00 | 45.00 | 45.00 |
| Ammonium laureth sulfate (25% active) | 10.00 | 10.00 | 10.00 | 10.00 | 10.00 |
| Dimethicone | 2.00 | 2.00 | 2.00 | 2.00 | 2.00 |
| Acrylate copolymer (27–30% active) (Acculyn ® 33) | — | 0.50 | 2.50 | 5.00 | 7.50 |
| Water | 40.85 | 40.35 | 38.35 | 35.85 | 33.35 |
| Adjuvants | 2.15 | 2.15 | 2.15 | 2.15 | 2.15 |
| TOTAL | 100.00 | 100.00 | 100.00 | 100.00 | 100.00 |

Examples 2–6 were prepared and stored at 50° C. for 30 days. After 30 days, examples 5 and 6 exhibited excellent stability, while examples 2 and 3 exhibited poor stability. Example 4 showed improved stability over examples 2 and 3 but not as good as examples 5 and 6. Examples 2–6 indicate that the acrylate copolymer alone successfully suspends silicone in shampoo compositions. These examples also demonstrate that a minimum amount of non-crosslinked suspending agent is required, without which the advantages of the present invention could not be obtained.

| INGREDIENTS | WEIGHT PERCENT |
|---|---|
| Ammonium lauryl sulfate (28% active) | 25.000 |
| Ammonium laureth sulfate (25% active) | 20.000 |

-continued

| INGREDIENTS | WEIGHT PERCENT |
|---|---|
| Sodium lauroyl sarcosinate (30% active) | 5.000 |
| Cocamidopropyl betaine (30% active) | 5.000 |
| Dimethicone | 2.000 |
| Cetyl alcohol | 0.200 |
| Stearyl alcohol | 0.100 |
| Acrylate copolymer (27–30% active) | |
| (Acculyn ® 33) | 7.200 |
| Purified water | 32.417 |
| Adjuvants | 3.083 |
| TOTAL | 100.000 |

Example 7 was stored at 50° C. for 30 days. To quantify the amount of silicone suspended throughout the sample after the 30-day period, 10 grams taken from the top of the sample was placed into a 50 ml centrifuge tube. To this was added approximately 20 ml of hexane, 1.5 grams sodium chloride and 20 ml of methanol. The sample was then centrifuged for approximately 30 minutes to break the emulsion. The hexane, which was the top layer, was evaporated in a hood to dryness and then weighed. The resulting solids were the silicone and adjuvants. It was determined that the adjuvants were also extracted by running a matrix blank (the same formula without dimethicone). The amount of silicone in the top layer was 1.97%±0.26. The process was repeated using 10 grams from the middle layer and 10 grams from the bottom layer. The amount of silicone in the middle layer was 2.22%±0.055. The amount of silicone in the bottom layer was 2.17%±0.0082. Thus, each layer contained about 2.00% indicating that the silicone was suspended throughout the entire strata of the shampoo composition.

Of course, it should be understood that a wide range of changes and modifications can be made to the embodiments described above. It is intended, therefore, that the foregoing description illustrates rather than limits this invention, and that it is the following claims, including all equivalents, that define this invention.

What is claimed is:

1. A shampoo composition comprising:
   (a) from about 1.00% to about 80.00% by weight of one or more surfactants selected from the group consisting of anionic, nonionic, cationic and zwitterionic surfactants and mixtures thereof;
   (b) from about 0.05% to about 15.00% by weight of one or more fatty alcohols having from about 10 to about 30 carbon atoms;
   (c) from about 0.10% to about 15.00% by weight of a non-volatile silicone; and
   (d) from about 1.35% to about 2.70% by weight of an acrylate copolymer suspending agent substantially free of crosslinking, wherein the suspending agent is the sole suspending agent for the silicone.

2. The shampoo composition of claim 1 wherein the surfactant is a mixture of anionic and zwitterionic surfactants.

3. The shampoo composition of claim 2 wherein the anionic surfactant is selected from the group consisting of alkyl sulfates, alkyl ether sulfates, sarcosinates, their salts, and mixtures thereof.

4. The shampoo composition of claim 3 wherein the alkyl sulfate has from about 12 to about 18 carbon atoms.

5. The shampoo composition of claim 3 wherein the alkyl portion of the alkyl ether sulfate has from about 12 to about 18 carbon atoms and the alkyl ether sulfate has from about 1 to about 6 moles of ethylene oxide.

6. The shampoo composition of claim 3 wherein the sarcosinate has from about 12 to about 18 carbon atoms.

7. The shampoo composition of claim 2 wherein the zwitterionic surfactant is selected from the group consisting of betaines, amido betaines, and amidosulfo betaines.

8. The shampoo composition of claim 1 wherein the non-volatile silicone is selected from the group consisting of polyalkyl siloxanes, polyalkylaryl siloxanes, polyether siloxane polymers, silicone gums, and mixtures thereof.

9. The shampoo composition of claim 8 wherein the non-volatile silicone has a viscosity of from about 5 to about 600,000 centistokes.

10. The shampoo composition of claim 8 wherein the non-volatile silicone is dimethicone.

11. The shampoo composition of claim 1 wherein the fatty alcohol is selected from alcohols having from about 12 to about 24 carbon atoms and combinations thereof.

12. The shampoo composition of claim 1 wherein the acrylate copolymer is a polymer of the ester of methacrylic acid and steareth-20 and one or more monomers of acrylic acid, methacrylic acid or one of their simple esters.

13. A shampoo composition comprising:
   (a) from about 5.00% to about 60.00% by weight of one or more surfactants selected from the group consisting of anionic, nonionic, cationic and zwitterionic surfactants and mixtures thereof;
   (b) from about 0.10% to about 10.00% by weight of one or more fatty alcohols having from about 12 to about 26 carbon atoms;
   (c) from about 1.00% to about 10.00% by weight of a non-volatile silicone; and
   (d) from about 2.00% to about 2.30% by weight of an acrylate copolymer substantially free of crosslinking, wherein the acrylate copolymer is the sole suspending agent for the silicone.

14. In a shampoo composition comprising water, one or more surfactants, one or more fatty alcohols, and a non-volatile silicone, the improvement comprising adding from about 1.35% to about 2.70% by weight of an acrylate copolymer suspending agent to suspend the non-volatile silicone in the composition, wherein the suspending agent is substantially free of crosslinking and wherein the suspending agent is the sole suspending agent for the silicone.

15. A method of shampooing the hair which comprises applying to the hair the composition of claim 1.

16. A method of shampooing the hair which comprises applying to the hair the composition of claim 13.

17. A method of suspending silicone in a shampoo composition comprising admixing from about 1.35% to about 2.70% by weight of an acrylate copolymer suspending agent in the shampoo composition, wherein the suspending agent is substantially free of crosslinking and wherein the suspending agent is the sole suspending agent for the silicone.

18. The method of claim 17 wherein the suspending agent is selected from the group consisting of an acrylate copolymer and a polymer of the ester of methacrylic acid and steareth-20 and one or more monomers of acrylic acid, methacrylic acid or one of their simple esters.

19. The method of claim 18 wherein the suspending agent is acrylate/steareth-20 methacrylate copolymer.

20. The method of claim 18 wherein the suspending agent is acrylate copolymer.

21. A method of suspending a non-volatile silicone in a shampoo composition that comprises water, one or more surfactants, and one or more fatty alcohols wherein the method includes the step of adding an effective amount of an acrylate copolymer suspending agent to the shampoo composition, wherein the suspending agent is substantially free of crosslinking and wherein the suspending agent is the sole suspending agent for the silicone.

22. The shampoo composition of claim 1 wherein the non-volatile silicone is directly incorporated into the composition.

23. The shampoo composition of claim 13 wherein the non-volatile silicone is directly incorporated into the composition.

24. The shampoo composition of claim 14 wherein the non-volatile silicone is directly incorporated into the composition.

25. The method of claim 17 wherein the non-volatile silicone is directly incorporated into the composition.

26. The method of claim 21 wherein the non-volatile silicone is directly incorporated into the composition.

* * * * *

UNITED STATES PATENT AND TRADEMARK OFFICE
CERTIFICATE OF CORRECTION

PATENT NO. : 5,968,493 Page 1 of 1
DATED : October 19, 1999
INVENTOR(S) : Jeffrey M. Dornoff It is certified that error appears in the above-identified patent and that said Letters Patent is hereby corrected as shown below:

<u>Title page,</u>
Item [56], References Cited, U.S. PATENT DOCUMENTS insert:
-- 5,294,435   3/1994   Remz
   5,674,509   10/1997   Date et al. --.
FOREIGN PATENT DOCUMENTS, insert:
-- 0 463 780 A2 1/1992   European Pat. Off. --.

<u>Column 9,</u>
Line 56, delete "anionicand" and substitute -- anionic and -- in its place.

Signed and Sealed this

Fourteenth Day of September, 2004

JON W. DUDAS
*Director of the United States Patent and Trademark Office*